United States Patent [19]

Pacella

[11] 4,265,236
[45] May 5, 1981

[54] PORTABLE INHALATOR DEVICE

[76] Inventor: Angelo M. Pacella, 39 Chute Rd., Dedham, Mass. 02026

[21] Appl. No.: 135,629

[22] Filed: Mar. 31, 1980

[51] Int. Cl.³ .......................................... A61M 15/00
[52] U.S. Cl. ........................... 128/203.23; 128/203.22; 128/203.15; 128/204.13; 128/202.13; 150/0.5
[58] Field of Search ..................... 128/203.15, 203.21, 128/203.22, 203.23, 203.24, 204.13, 204.14, 203.12, 204.17, 200.12; 46/220; 224/148; 273/425, 1 B; 63/15.7, 31, DIG. 2, 3; 150/0.5; 239/33

[56] References Cited

U.S. PATENT DOCUMENTS

| 330,970 | 11/1885 | Ellis | 128/204.13 |
|---|---|---|---|
| 419,942 | 1/1890 | Harding | 128/266 |
| 1,062,786 | 5/1913 | Miller | 239/33 |
| 1,905,752 | 4/1933 | Rees | 128/266 |
| 2,086,588 | 7/1937 | Tobin et al. | 128/204.13 |
| 3,332,166 | 7/1967 | Alexander | 272/1 B |
| 3,517,884 | 8/1970 | Harvath | 239/33 |
| 3,828,577 | 8/1974 | Haymes | 128/204.12 X |
| 3,881,277 | 5/1975 | Delph et al. | 46/220 |
| 4,062,359 | 12/1977 | Geaghan | 128/203.12 X |
| 4,208,888 | 6/1980 | Erdman et al. | 63/31 |

FOREIGN PATENT DOCUMENTS

| 2300517 | 12/1975 | France | 63/31 |
|---|---|---|---|
| 204657 | 10/1923 | United Kingdom | 63/DIG. 2 |

OTHER PUBLICATIONS

Argo Industries Corp., "Water Fun–No. 536 Underwater Diving Rings", Mar. 10, 1965.

Primary Examiner—Henry J. Recla
Attorney, Agent, or Firm—Joseph S. Iandiorio

[57] ABSTRACT

A portable inhalator device including a length of flexible tubing; a frictional engaging area on the outer surface of a first end of the tubing; and a second engaging area on the inner surface of the second end of the tubing, for releasably gripping the first end of the tubing and sealingly engaging therewith to form a closed loop.

19 Claims, 4 Drawing Figures

PORTABLE INHALATOR DEVICE

FIELD OF INVENTION

This invention relates to a portable inhalator, and more particularly to such an inhalator which forms a sealed closure and which may be used to carry a dose of inhalant.

BACKGROUND OF INVENTION

Inhalators are used to introduce into the nasal passages a substance which is a fluid or may be borne by a fluid, e.g. powder. Typically such devices have a special fixture at one end to cooperate with the human nostril and another fixture at the other end to hold the substance to be inhaled, the inhalant. Alternatively, there may be provided at the nostril engaging end a space to hold the inhalant. Such apparatus tends to be large, cumbersome, and not very attractive or convenient to carry about or to use. In addition, very often the entire charge or dose of inhalant is not delivered. Some would be trapped where the flushing air could not reach to flush the powder. Further the delivery to the nostril is often a narrow stream which does not distribute the inhalant well.

SUMMARY OF INVENTION

It is therefore an object of this invention to provide an improved inhalator device which is simple, compact, and inexpensive.

It is further object of this invention to provide such an inhalator device which is easy to carry and attractive and may be worn as a part of one's apparel or jewelry.

It is a further object of this invention to provide such an inhalator device which has an improved scouring agent to remove all of the inhalant from the inhalator device and improved distribution of the inhalant in the nostril.

It is a further object of this invention to provide such an inhalator device which enables a dose of inhalant to be safely stored and carried in it.

It is a further object of this invention to provide such an inhalator device which allows for measurement of specific dosages in the inhalator.

The invention features a portable inhalator device made from a length of flexible tubing. There is a frictional engaging area on the outer surface of the first end of the tubing, and the second end of the tubing has a second engaging area on the inner surface for releasably gripping the first end of the tubing. The two ends sealingly engage each other to form a closed loop.

In a preferred embodiment, the second end may be resiliently expandable or permanently enlarged to snugly receive the first end. The inner surface of the second end may include ridges to better grip the frictional engaging area of the first end. The first end may be rounded for enabling easy insertion thereof into the second end and also into the nostril of the user. The tubing may include a space for holding a dose of inhalant, and the tubing may also include calibrations for indicating the amount of inhalant contained in the tubing. The tubing is at least partially transparent in the area of calibration for viewing the dosage present. Securing means may be provided for attaching the inhalator device to jewelry or other apparel worn by the user. The securing means may be a simple eye or other means to attach a chain to the tubing, or may be a sleeve or similar element which grips the sleeve and may be gaily decorated to enhance its attractiveness.

There may be flow control means disposed in the tubing for controlling the flow of air into the tubing and controlling the flow of air and inhalant out of the tubing and into the nose of the inhaler. The flow control means may include some means for including turbulence in the flow through the tubing to improve the distribution of the dosage as it is dispensed. The means for inducing turbulence may include one or more spiral ridges in the tube, for example carried on the inner surface of a cylindrical insert.

The inhalator device may also be made with frictional engaging areas on each end of the tubing which interconnect with a coupling that has an opening at each end for releasably gripping the outer surfaces of the ends of the tubing and sealingly engaging them to form a closed loop.

DISCLOSURE OF PREFERRED EMBODIMENT

Other objects, features and advantages will occur from the following description of a preferred embodiment and the accompanying drawings, in which.

Figure 1:
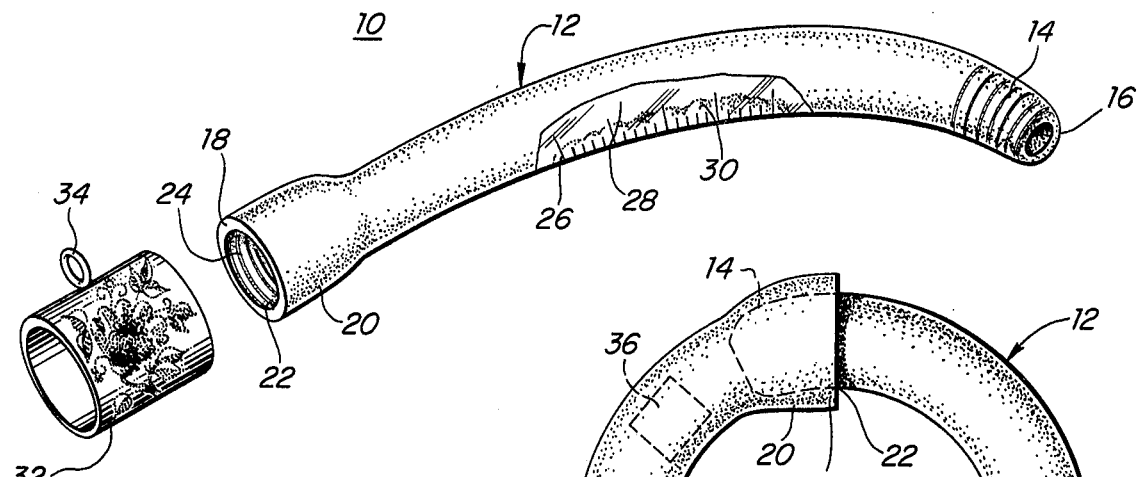
FIG. 1 is an axonometric view of an inhalator device according to this invention and securing means in the form of a decorative collar.

The invention may be accomplished with a portable inhalator device formed of a length of tubing such as polyethylene vinyl chloride. A frictional engaging area is provided on the outer surface of a first end of the tubing, such as by scoring or roughening on the end of the tubing. A second engaging area is provided on the inner surface of the second end of the tubing. This may be permanently expanded or may be resiliently expandable for releasably gripping the first end of the tube and sealingly engaging with it to form a closed loop. This enables the device to additionally act as a storage facility for a dose of inhalant, which may be in the form of a fluid or fluid-like substance, for example a liquid, a gas, or a powder, which can be flushed through the tubing and delivered through the vehicle of some liquid or gas medium. The inner surface of the enlarged or enlargable second end may include ridges or some other means to improve the gripping of the first end of the tubing which bears the frictional engaging area. Typically the first end is rounded somewhat to enable easy insertion of that first end into the second end, and also into the nostril of the user. The tubing itself provides a space for holding a dose of the inhalant. Preferably, the tubing also includes calibrations for indicating the amount of inhalant contained in the tubing. The tubing is at least partially transparent in the area of calibration to enable viewing of the dosage which is present.

Some securing means is typically provided for attaching the inhalator device to jewelry or other apparel. For example, a ring or some similar element may be made integral with the tubing to receive a chain or other means of attachment. Alternatively, a collar which may be gaily decorated may be provided which fits over a portion of the tubing and includes some attachment device such as a ring for attachment purposes. The inhalator device may be worn by itself as a bracelet, clamped directly around the wrist, to remind the user of inhalant taken, or to be taken.

A flow control means may be disposed in the tubing for controlling the flow into the tubing, and also controlling the flow of the inhalant out of the tubing. The flow control means typically induces some turbulence in the flow through the tubing in order to more properly scavenge the inhalant from the tubing, and also to provide better distribution at delivery to the nostril of the user. Further, the means for inducing the turbulence may include a spiral ridge or ridges, for example on the inside of a hollow cylinder which fits inside the tubing.

It is also considered that the inhalator device of this invention may include a length of flexible tubing with frictional engaging areas on each end which engage with a coupling sleeve. The coupling sleeve has an opening at each of its ends for gripping the outer surfaces of the ends of the tubing that contain the frictional engaging area. In this manner the two ends are sealingly engaged with the coupling sleeve to form a closed loop.

There is shown in FIG. 1 an inhalator device 10 according to this invention including a length of tubing 12 having a frictional engaging area 14 formed by scoring on a first end 16, and an enlarged portion 18 on the other end 20 whose internal surface 22 receives frictional engaging area 14 of end 16. Internal surface 22 may include a plurality of ridges 24 to further improve the engagement with engaging area 14. Calibrations 26 in a transparent area 28 of tubing 12 are provided in order to judge the amount of inhalant 30 which constitutes the dosage presently stored in tubing 12.

For convenience some securing means, such as a decorative collar 32, may be provided to snugly fit about enlarged end 18. Collar 32 has an eye ring 34 which may receive a chain or other means for attachment to jewelry or apparel of the user. End 16 is rounded in order to facilitate engagement with surface 22 as well as the nostril of the user.

Figure 2:
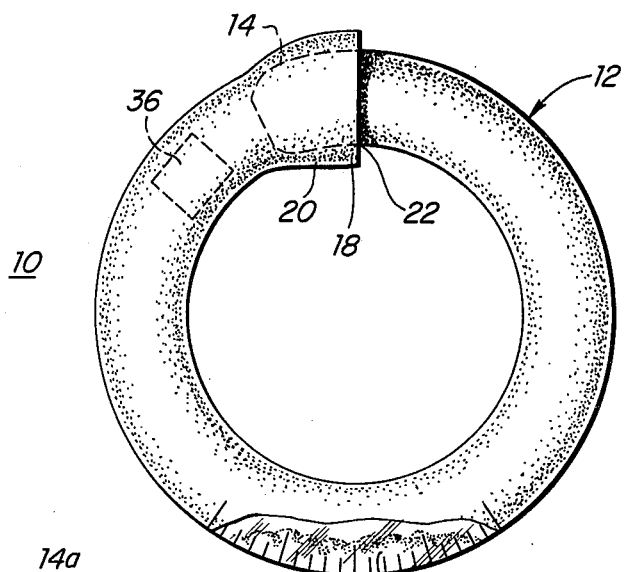
FIG. 2 is a plan view of the device of FIG. 1 in the closed position and including a flow control device according to this invention.

In the closed condition, FIG. 2, end 14 of tubing 12 is snugly and sealingly engaged in recess 22 of end 18 to form a closed storage area in which the dose of inhalant 30 is safe from loss. A flow control device 36 is located within tubing 12 to enhance the emptying and distribution of the inhalant.

Figure 3:
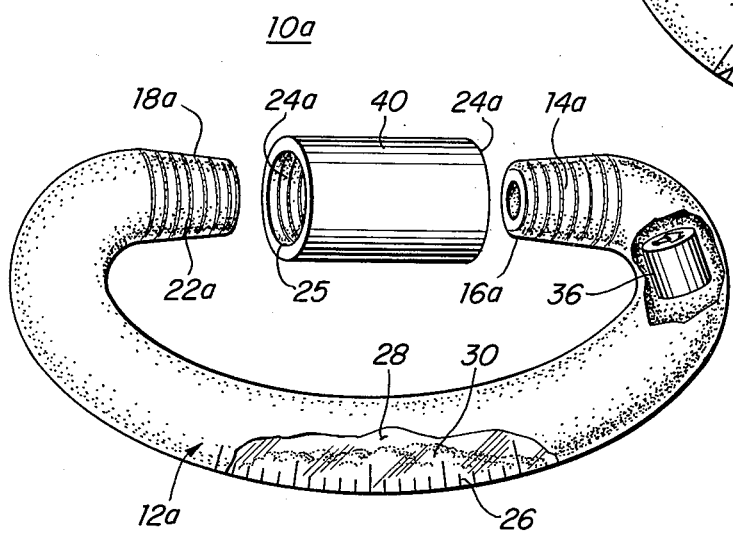
FIG. 3 is an axonometric view of another construction in which the tubing interconnects with a coupling sleeve.

Alternatively, both ends 14a, 18a, FIG. 3, of tubing 12a may have frictional engaging surfaces 16a, 22a, which engage with scored areas 24a in recesses 25 at either end of coupling sleeve 40. Both ends 14a and 18a are rounded to facilitate engagement with coupling sleeve 40 and with the nostril of the user.

Figure 4:
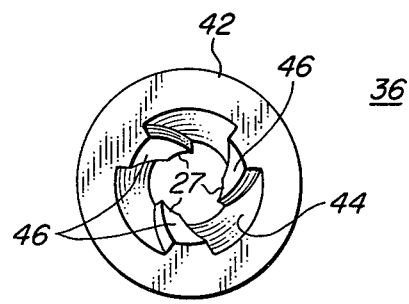
FIG. 4 is a perspective view looking into a flow control device having spiral ridges.

Flow control device 36 may include a piece of pipe 42, FIG. 4, that fits inside of tubing 12a and includes on its inner surface 44 a spiral ridge or ridges 46 which induce a measure of turbulence into the fluid or fluid-powder medium to ensure complete removal and proper distribution of the inhalant.

Other embodiments will occur to those skilled in the art and are within the following claims:

What is claimed is:
1. A portable inhalator device comprising:
a length of flexible tubing;
a frictional engaging area on the outer surface of a first end of said tubing;
a second engaging area on the inner surface of the second end of said tubing for releasably gripping said first end of said tubing and sealingly engaging therewith to form a closed loop
means on said first end of said tubing for insertion into a breathing passage of a user and into said second end; and
means within said tubing for holding inhalant for affecting the flow of air therethrough whereby when said first end is gripped in said second end, the tubing acts as a storage vessel and when said ends are separated, the tubing acts as an inhalator.

2. The inhalator device of claim 1 in which said second end is permanently enlarged to snugly receive said first end.

3. The inhalator device of claim 1 in which said inner surface of said second end includes ridges.

4. The inhalator device of claim 1 in which said means for insertion comprises said first end being rounded for enabling easy insertion thereof into said second end and the nostril of a user.

5. The inhalator device of claim 1 in which said means for holding inhalant within said tubing includes a space for holding a dose of inhalant.

6. The inhalator device of claim 1 in which said tubing includes calibrations for indicating the amount of inhalant contained in said tubing and said tubing is at least partially transparent in the area of calibration for viewing the dosage present.

7. The inhalator device of claim 1 further including securing means for attaching to jewelry and apparel.

8. The inhalator device of claim 1 further including flow control means disposed in said tubing for controlling flow of fluid into and of fluid and inhalant out of said tubing.

9. The inhalator device of claim 8 in which said flow control means includes means for inducing turbulence in the flow through said tubing.

10. The inhalator device of claim 9 in which said means for inducing turbulence includes a spiral ridge.

11. A portable inhalator device comprising:
a length of flexible tubing;
a frictional engaging area on the outer surface of each end of said tubing;
a coupling sleeve having an opening at each end for releasably gripping said outer surfaces of said ends of said tubing and sealingly engaging therewith to form a closed loop
means on each end of said tubing for insertion into a breathing passage of a user and into each end of said sleeve; and
means within said tubing for holding inhalant for affecting the flow of air therethrough whereby when said ends of said tubing are gripped in said ends of said sleeve, the tubing acts as a storage vessel and when said ends of said tubing are separated from the ends of said sleeve, the tubing acts as an inhalator.

12. The inhalator device of claim 11 in which the inner surfaces of said sleeve openings include ridges.

13. The inhalator device of claim 11 in which said ends are rounded for enabling insertion thereof into said sleeve opening.

14. The inhalator device of claim 11 in which said means for holding inhalant within said tubing includes a space for holding a dose of inhalant.

15. The inhalator device of claim 11 in which said tubing includes calibrations for indicating the amount of inhalant contained in said tubing and said tubing is at least partially transparent in the area of calibration for viewing the dosage present.

16. The inhalator device of claim 11 in which said sleeve includes securing means for attaching to jewelry and apparel.

17. The inhalator device of claim 11 further including flow control means disposed in said tubing for controlling flow of fluid into and of fluid and inhalant out of said tubing.

18. The inhalator device of claim 17 in which said flow control means includes means for inducing turbulence in the flow through said tubing.

19. The inhalator device of claim 18 in which said means for inducing turbulence includes a spiral ridge.

* * * * *